United States Patent
Leflaive et al.

(10) Patent No.: US 9,145,343 B2
(45) Date of Patent: Sep. 29, 2015

(54) PROCESS AND APPARATUS FOR THE SIMULATED COUNTER-CURRENT PRODUCTION OF PARA-XYLENE, CONSTITUTED BY TWO ADSORBERS IN SERIES WITH A TOTAL NUMBER OF 22 OR FEWER BEDS

(71) Applicant: IFP Energies nouvelles, Rueil-Malmaison Cedex (FR)

(72) Inventors: Philibert Leflaive, Mions (FR); Damien Leinekugel le Cocq, Lyons (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 115 days.

(21) Appl. No.: 14/064,884

(22) Filed: Oct. 28, 2013

(65) Prior Publication Data

US 2014/0121436 A1    May 1, 2014

(30) Foreign Application Priority Data

Oct. 26, 2012  (FR) ...................................... 12 02869

(51) Int. Cl.
*C07C 7/12* (2006.01)
*C07C 7/13* (2006.01)
*B01D 15/18* (2006.01)

(52) U.S. Cl.
CPC .............. *C07C 7/12* (2013.01); *B01D 15/1828* (2013.01); *C07C 7/13* (2013.01)

(58) Field of Classification Search
None
See application file for complete search history.

(56) References Cited

U.S. PATENT DOCUMENTS

| 5,629,467 | A  | * | 5/1997  | Hotier et al. ................. 585/805 |
| 5,972,224 | A  |   | 10/1999 | Hotier et al. |
| 6,110,364 | A  |   | 8/2000  | Hotier et al. |
| 6,376,734 | B1 |   | 4/2002  | Magne-Drisch et al. |
| 7,759,534 | B2 |   | 7/2010  | Leflaive et al. |
| 7,838,714 | B2 |   | 11/2010 | Leflaive et al. |
| 2009/0018380 | A1 |   | 1/2009 | Leflaive et al. |
| 2009/0036726 | A1 |   | 2/2009 | Leflaive et al. |
| 2011/0315634 | A1 | * | 12/2011 | Hotier et al. ................. 210/659 |
| 2012/0302812 | A1 | * | 11/2012 | Corradi et al. ................ 585/821 |
| 2013/0006031 | A1 | * | 1/2013  | Leflaive et al. .............. 585/821 |
| 2013/0053610 | A1 | * | 2/2013  | Leinekugel le Cocq et al. ............. 585/855 |

FOREIGN PATENT DOCUMENTS

| EP | 0923970 A1 | 6/1999 |
| FR | 2693186 A1 | 1/1994 |
| FR | 2795407 A1 | 12/2000 |
| FR | 2919603 A1 | 2/2009 |
| FR | 2919604 A1 | 2/2009 |

OTHER PUBLICATIONS

Search Report for FR1202869 dated Jun. 13, 2013.
Inst Francais Du Petrole, "Sepn. and recovery of para-xylene," Espacenet, Publication Date: Jan. 7, 1994; English Abstract of FR2693186.

* cited by examiner

*Primary Examiner* — Tam M Nguyen
(74) *Attorney, Agent, or Firm* — Millen, White, Zelano & Branigan, P.C.

(57) ABSTRACT

The present invention describes a novel configuration for simulated counter-current para-xylene production units, constituted by two adsorbers, characterized in that the volume occupied by the solid adsorbent is reduced by at least 8% compared with the volume of solid adsorbent contained in the adsorbers of a prior art unit. This novel configuration can be used to minimize the quantity of solid adsorbent necessary to produce a given quantity of para-xylene.

16 Claims, 3 Drawing Sheets

PROCESS AND APPARATUS FOR THE SIMULATED COUNTER-CURRENT PRODUCTION OF PARA-XYLENE, CONSTITUTED BY TWO ADSORBERS IN SERIES WITH A TOTAL NUMBER OF 22 OR FEWER BEDS

FIELD OF THE INVENTION

The invention relates to the field of separating para-xylene from other aromatic C8 isomers. To carry out such separation, a family of processes and associated devices is used, which is known under the name of simulated moving bed separation processes or simulated counter-current separation, or as the VARICOL process; we shall hereinafter use the general term of SCC (abbreviation of simulated counter-current) separation processes.

PRIOR ART

SCC separation is well known in the art. As a general rule, a para-xylene separation process functioning in simulated counter-current mode comprises at least four zones, and possibly five or six, each of those zones being constituted by a certain number of successive beds, and each zone being defined by its position included between a supply point and a withdrawal point. Typically, a SCC unit for the production of para-xylene is supplied by at least one feed F to be fractionated (containing para-xylene and the other aromatic C8 isomers) and a desorbant D, occasionally termed the eluent (generally para-diethylbenzene or toluene), and from said unit at least one raffinate R containing the isomers of para-xylene and desorbant and an extract E containing para-xylene and desorbant are withdrawn.

Other injection or withdrawal points may be added in order to rinse the distribution circuits, as described, for example, in U.S. Pat. No. 7,208,651, the addition of such supplemental rinsing streams does not in any way change the principle of the function of the SCC. For the sake of clarity, we shall not add these supplemental injection and withdrawal points to the description of the process of the invention.

The supply and withdrawal points are modified over time, shifted in the same direction by a value corresponding to one bed. The various injection or withdrawal points may be shifted either simultaneously or non-simultaneously, as disclosed in U.S. Pat. No. 6,136,198. The process in accordance with this second functional mode is known as the VARICOL process.

In general, four different chromatographic zones are defined in a SCC unit:
  zone 1: para-xylene desorption zone, included between the injection of desorbant D and the removal of extract E;
  zone 2: isomers of para-xylene desorption zone, included between the removal of the extract E and the injection of the feed to be fractionated F;
  zone 3: para-xylene adsorption zone, included between the injection of the feed and the withdrawal of the raffinate R;
  zone 4: zone located between the withdrawal of the raffinate R and the injection of the desorbant D.

As described by Lim et al (2010, Ind Eng Chem Res, vol 49, p 3316-3327), the process for the separation of para-xylene by SCC is generally composed of 24 beds, distributed among two adsorbers each containing 12 beds. The 2 adsorbers are connected in series, and the SCC cycle thus comprises 24 steps during which each stream (D, E, F, R) is injected or withdrawn downstream of each of the 24 beds.

The term "connection in series" of two adsorbers each of twelve beds means the following 3 features:
  the bed at the foot of the first adsorber is connected to the bed at the head of the second adsorber via a line containing at least one recirculation pump and possibly other equipment such as a flow meter, a pressure sensor, etc.;
  the bed at the foot of the second adsorber is connected to the bed at the head of the first adsorber via a line containing at least one recirculation pump and possibly other equipment such as a flow meter, a pressure sensor, etc.;
  the assembly of the two adsorbers has 1 point for introducing feed, 1 point for introducing eluent, 1 point for withdrawing raffinate and 1 point for withdrawing extract.

Very generally, an adsorber is a cylindrical column in which beds of adsorbent are disposed one above the other and separated by distributor plates known as intermediate plates. When the dimensions of the columns concerned are large (between 3 and 15 meters in diameter, for example), networks with varying degrees of branching are often used to channel the fluids from outside the column to the various plates of the multi-stage column.

Such distribution networks may be fairly bulky, and so such networks are routinely positioned in the adsorbent bed itself in order to minimize the total volume of the column.

A generally hemispherical volume is positioned above the head bed of adsorbent.

This volume will hereinafter be termed the head dome. A distributor plate known as the head plate separates the head bed of adsorbent from the volume of the head dome. A distributor plate known as the head plate separates the bed of adsorbent from the volume of the head dome. A specific distribution network which also employs lines with varying degrees of branching is used to channel the fluids from the recirculation line originating in the other adsorber to the head plate of the adsorber under consideration.

This distribution network, which we shall designate the head octopus manifold, is located in the volume of the head dome.

A generally hemispherical volume is located below the bottom bed of adsorbent.

This volume will hereinafter be termed the bottom dome space. A distributor plate known as the bottom plate separates the bottom bed of adsorbent from the bottom dome space.

A specific distribution network also using lines with a varying degree of branching is used to channel the fluids from the bottom plate of the adsorber under consideration to the recirculation line supplying the other adsorber. This distribution network, which we shall designate the bottom octopus manifold, is located in the bottom dome space.

Furthermore, research aimed at developing novel adsorbents for separating xylenes can be used to envisage very significant gains in performance. The simplest means for benefiting from the gains in performance of these novel adsorbents consists of increasing the flow rates in SCC units in order to increase the productivity for constant purity and yield of para-xylene.

The increase in the internal circulation causes a rise in the pressure drops within a SCC process. However, the pressure drops play an important role in sizing the recirculation pump or pumps, the thickness of the adsorber walls, the size of the support systems for the distributor plates, etc.

An increase in the interstitial velocity may also play a very important role as regards the mechanical behaviour of the grains of adsorbent which, when they deteriorate, may become a limiting factor in operating a SCC unit.

The increase in the productivity in an existing unit will thus be necessarily limited.

That limitation in the productivity of processes for producing para-xylene by SCC is known from the prior art (in particular from U.S. Pat. No. 7,649,124 and U.S. Pat. No. 7,635,795) and solutions have been proposed to improve this process:

patents FR 2 743 068 and U.S. Pat. No. 7,635,795 present processes using several adsorption steps. The first step is intended to produce a stream enriched in para-xylene with a purity insufficient to allow it to be used commercially (<99% by weight). The second step can be used to obtain very high purity para-xylene. In particular, FIG. 5 of U.S. Pat. No. 7,635,795 illustrates the debottlenecking of a pre-existing 24-bed SCC unit by adding an adsorber for pre-treating the feed;

patents FR 2 693 186, FR 2 757 507 and U.S. Pat. No. 7,649,124 present processes using a step for SCC adsorption in combination with crystallization. The first step is intended to produce, by SCC, a stream enriched in para-xylene with a purity which is insufficient to allow it to be used commercially (typically of the order of 90% by weight). The second step can be used to obtain very high purity para-xylene by crystallization. In particular, FIG. 5 of U.S. Pat. No. 7,649,124 illustrates the debottlenecking of a pre-existing 24-bed SCC unit (composed of two 12-bed adsorbers) by means of a modification to an adsorption process using two adsorbers in parallel and by adding a crystallization step to post-treat the extracts.

All of the solutions recommended in the prior art to solve the problem of limiting the productivity of units for the production of para-xylene using a 24-bed simulated moving bed thus consists of adding a separation stage either using an adsorber to pre-treat the feed and/or a post-treatment of the extract(s) by crystallization, giving rise to very substantial costs.

Those solutions also suffer from the disadvantage of only allowing the productivity to be increased by significantly increasing the quantity of para-xylene produced and thus the quantity of feed introduced into the complex, which is not always possible. They also have the disadvantage of systematically necessitating a substantial investment.

Another possibility is to reduce the quantity of adsorbent in the adsorbers while maintaining the quantity of para-xylene produced. In order to reduce the quantity of adsorbent in the adsorbers, one possibility is to partly fill each bed of the SCC unit. The space between the surface of each bed of adsorbent and the upper distributor plate is thus increased. While that solution provides satisfactory results when the quantity of adsorbent is reduced by a few percent, that solution is not appropriate when the quantity of sieve removed from each bed is more than 10%. In fact, the "void" zone contained between the plate and the bed of adsorbent is then too big and causes recirculation, which deleteriously affects the plug flow nature of the flow, resulting in drops in the purity of the para-xylene produced and in the yield.

The process of the invention proposes overcoming the problem by limiting productivity of the para-xylene production units composed of two adsorbers by reducing the number of beds in each adsorber, in order to produce the same quantity of high purity para-xylene (i.e. more than 99.7%) with a reduced volume of solid adsorbent.

It has in fact surprisingly been shown that the use of two adsorbers containing fewer than 12 beds, which is the conventional number of beds per adsorber for the production of para-xylene by SCC, with appropriate operating conditions (configuration, switch period, flow rates, water content in adsorbent, temperature and quantity of solvent) can permit the production of a commercial purity quantity of para-xylene (i.e. more than 99.7% by weight) identical to the quantity produced by the unit using two conventional adsorbers each containing 12 beds filled with solid adsorbent.

It has also been shown that the modifications to be made to a unit constituted by 2 adsorbers each containing 12 beds in order to obtain the process or the unit of the invention were relatively slight, and did not necessitate substantial investment.

Thus, the present invention is particularly suitable for the case when revamping is desired of a unit constituted by two adsorbers each with 12 beds into a unit with a reduced number of beds, thereby meaning that the quantity of solid adsorbent in the unit can be minimized.

BRIEF DESCRIPTION OF THE FIGURES

The two adsorbers are associated in series, while the device operates in a single 16-step cycle.

BRIEF DESCRIPTION OF THE INVENTION

Figure 1:
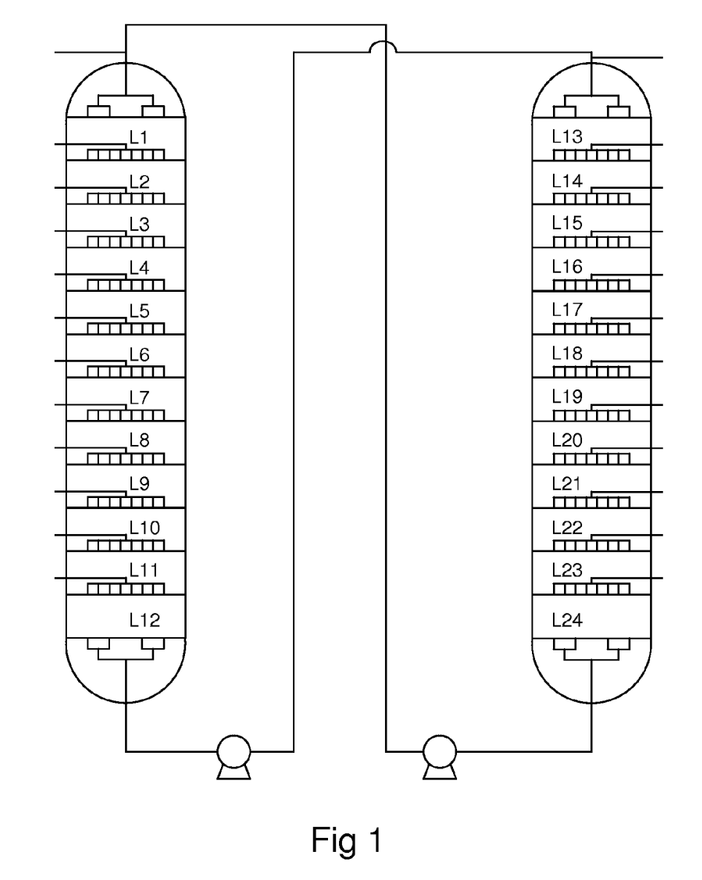
FIG. 1 represents the prior art process comprising two adsorbers each with twelve beds, associated in series.
Figure 2:
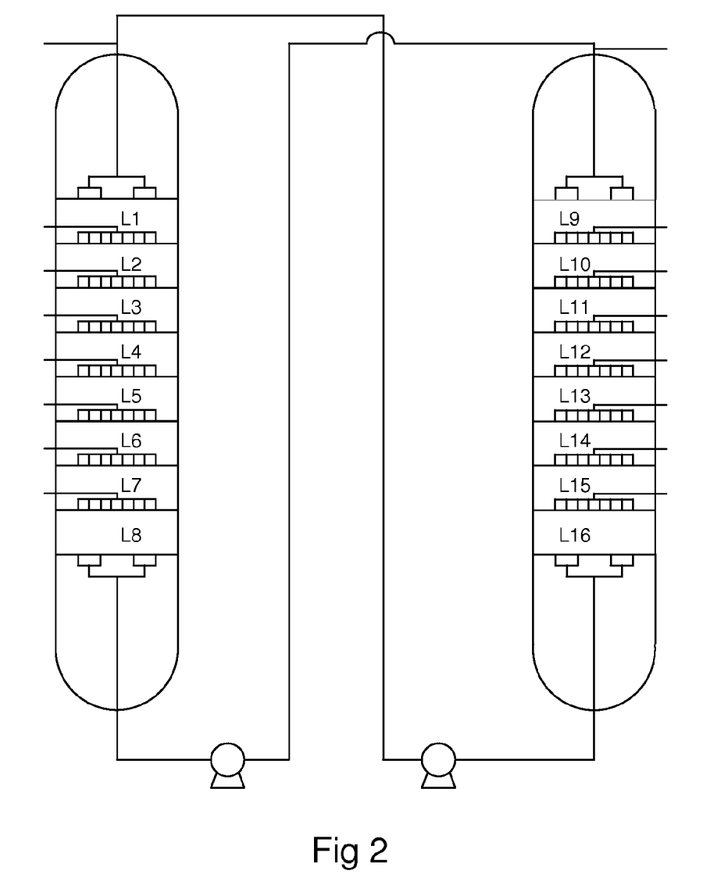
FIG. 2 represents the device of the invention in a particular case constituted by two adsorbers each with 8 beds, i.e. a total of 16 beds (L1 to L16).
Figure 3:
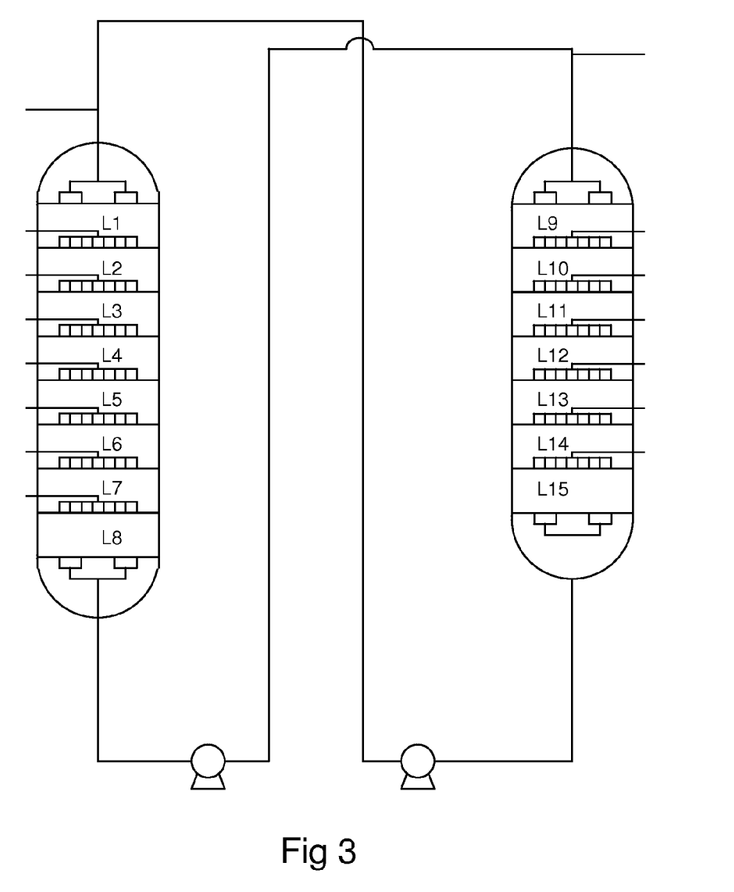
FIG. 3 represents the device of the invention in the particular case constituted by two adsorbers, one containing 8 beds, the second containing 7 beds, i.e. a total of 15 beds (L1 to L15). The two adsorbers are associated in series, while the device operates in a single 15-step cycle.

The present invention concerns a process for separating para-xylene from a feed F essentially comprising para-xylene and its aromatic C8 isomers, constituted by two adsorbers operating in series.

The process of the invention is constituted by two adsorbers connected in series with a total number of beds of 22 or fewer. Each adsorber has a number of beds of 12 or fewer. If one of the adsorbers of the process of the invention effectively has 12 beds, then the number of beds in the second adsorber is 10 or fewer.

The fact of retaining two adsorbers (instead of optionally having only a single adsorber comprising the total number of beds) has the advantage of limiting the variation in pressure per adsorber by distributing it over the two adsorbers in a manner so as to limit the pressure at the head of each of the adsorbers. The minimum bottom pressure of the adsorbers has to be at least equal to the bubble pressure of the most volatile compound at the temperature of the unit, in order to maintain a liquid phase at every point of the unit.

More precisely, the present invention covers two distinct cases which depend on the industrial starting situation:

case 1: the process of the invention is carried out using a new unit;

case 2: a para-xylene separation unit already exists, constituted by two adsorbers each with 12 beds (unit which is sometimes known as a 24 bed unit) and this unit is to be transformed in order to obtain a unit in accordance with the invention by reducing the number of beds.

In the case of a new unit, the present invention can be defined as a process for separating xylenes by simulated counter-current (SCC) using two adsorbers, the process containing a total number of beds Nt of 22 or fewer, and preferably a total number of beds Nt of 18 or fewer, said process having a line for introducing feed (F), a line for introducing eluent (D), a line for withdrawing extract (E) and a line for withdrawing raffinate (R) and being divided into 4 chromatographic zones defined as follows:

zone 1: para-xylene desorption zone, included between the injection of desorbant D and the removal of extract E;
zone 2: isomers of para-xylene desorption zone, included between the removal of the extract E and the injection of the feed to be fractionated F;
zone 3: para-xylene adsorption zone, included between the injection of the feed and the withdrawal of the raffinate R;
zone 4: zone located between the withdrawal of the raffinate and the injection of the desorbant;

and the two adsorbers functioning in series, i.e. the last bed of the first adsorber is connected to the first bed of the second adsorber via a line containing a recirculation pump and the last bed of the second adsorber is connected to the first bed of the first adsorber via a line containing a recirculation pump which is distinct from the preceding pump.

In accordance with first variation of the process of the invention, the number of beds N1 of the first adsorber and the number of beds N2 of the second adsorber are equal.

In the most general case, the number of beds of the first adsorber and the number of beds of the second adsorber are different.

In a second variation of the process of the invention, the number of beds N1 of the first adsorber is equal to 12.

When remodelling an existing unit, the present invention can be defined as a process for separating xylenes by simulated counter-current (SCC) using an existing unit composed of two adsorbers each containing 12 beds, which unit is transformed to finally contain a total number of beds Nt of 22 or fewer, and said unit having a line for introducing feed (F), a line for introducing eluent (D), a line for withdrawing extract (E) and a line for withdrawing raffinate (R) and being divided into 4 chromatographic zones defined as follows:

zone 1: para-xylene desorption zone, included between the injection of desorbant D and the removal of extract E;
zone 2: isomers of para-xylene desorption zone, included between the removal of the extract E and the injection of the feed to be fractionated F;
zone 3: para-xylene adsorption zone, included between the injection of the feed and the withdrawal of the raffinate R;
zone 4: zone located between the withdrawal of the raffinate and the injection of the desorbant;

and the two adsorbers functioning in series, i.e. the last bed of the first adsorber is connected to the first bed of the second adsorber via a line containing a recirculation pump and the last bed of the second adsorber is connected to the first bed of the first adsorber via a line containing a recirculation pump which is distinct from the preceding pump, and the beds of each adsorber constituting a compact assembly in that there are no void spaces which are capable of accepting an existing bed between the beds of each adsorber.

The beds are numbered from top to bottom, the first bed being the head bed.

In more detail, the set of adsorption beds of a given adsorber can be considered to form a compact assembly, which means that the beds which have been removed are beds which were located at the ends of the adsorber in the remodelled unit.

In accordance with a first variation of the process of the invention, in its configuration of remodelling an existing unit, the plugged inlets and outlets are all located above the head plate.

In a second variation of the process of the invention, in its configuration of remodelling an existing unit, the plugged inlets and outlets are all located below the head plate.

The present invention also concerns a method for remodelling an existing unit with two adsorbers each with 12 beds, into a unit with two adsorbers connected in series with a total number of beds of 22 or fewer which comprises the following steps:

displacing the head and/or bottom plates of at least one of the adsorbers by a height corresponding to the number of beds of adsorbents removed at the head and/or the bottom;
removing the intermediate networks and plates corresponding to the removed beds;
plugging the inlet/outlet devices corresponding to the removed networks;
modifying the head octopus manifolds and/or bottom octopus manifolds in order to respectively supply the head plate and/or collector plate from the bottom plate when the position thereof has been modified.

The term "when the position thereof has been modified" is defined because in the context of the present invention, just one of the two adsorbers may have its number of beds reduced, the other retaining its initial number of 12 beds.

DETAILED DESCRIPTION OF THE INVENTION

In the remainder of the text, in order to avoid any ambiguity, we shall state whether we are in the first situation (new unit) or in the second situation (remodelled unit).

When no statement is given as to the case under consideration, the information provided will be valid for both cases.

The adsorbers of the unit of the invention each contain a plurality of beds separated by plates Pi with a chamber for distribution and/or extraction of fluids in or from the various beds of adsorbent, and programmed means for sequential distribution and extraction of fluids.

Said programmed means for sequential distribution and extraction of fluids are typically one of the following two major types of technology:

either for each plate, a plurality of programmed on-off valves for supply or withdrawal of fluids, these valves typically being located in the immediate vicinity of the corresponding plate, and for each plate Pi comprising at least 4 programmed 2-way on-off valves respectively for the 2 supplies of fluids F and D and the 2 withdrawals of fluids E and R;
or a rotary multi-way valve for supply or withdrawal of fluids over all of the plates.

The adsorption step of the process of the invention requires devices for rinsing the injection and withdrawal networks in order to obtain a para-xylene purity of 99.7% by weight or more.

Two cases can be distinguished regarding the network rinsing devices which might be employed in the process of the invention:

the first device consists of flushing the injection/withdrawal network of a given plate with desorbant or relatively pure para-xylene. To this end, for example, a stream is withdrawn from zone 1 (so that the network associated with zone 1 can be flushed) and said stream is re-injected into zone 2 (so that the network associated with zone 2 can be flushed). It is also possible to inject a small stream of extract or para-xylene after distillation into the plate of zone 2 closest to the extract withdrawal point. Other possibilities for rinsing by injection and withdrawal are possible. Such devices have been described, in particular in U.S. Pat. No. 3,201,491, U.S. Pat. No. 5,750,820, U.S. Pat. No. 5,912,395, U.S. Pat. No. 6,149,874 and WO 2006/096394. Preferably, this rinsing device will be employed when the supply or withdrawal of fluids over all of the plates is carried out using a rotary multi-way valve;

the second device consists of passing a majority of the principal stream into the interior of the adsorber and a minority of that stream (typically 1% to 20% of the principal stream) to the outside via external bypass lines between successive plates. This flushing of the injection/withdrawal network at a plate by a stream originating from the upper plate is typically carried out continuously such that the lines and zones of the injection/withdrawal network are no longer "dead" but are constantly flushed. Such devices have in particular been described in patents FR 2 935 100, FR 2 935 101 and FR 2 944 215. Preferably, this rinsing device will be employed when supply or withdrawal of the fluids over all of the plates is carried out via a plurality of programmed on-off valves.

In accordance with one feature of the process of the invention, the adsorbent used in the adsorption step may comprise a faujasite type zeolite exchanged with barium or exchanged with barium and potassium.

Preferably, the adsorbent is an agglomerated zeolitic adsorbent solid comprising small crystals (i.e. with a diameter of 2 µm or less) of X zeolite at least 90% exchanged either by barium ions alone or by barium ions and potassium ions, the exchangeable sites occupied by potassium representing up to ⅓ of the exchangeable sites occupied by the barium+potassium ions (any complement generally being provided by alkali or alkaline-earth ions other than barium and potassium). The small crystals also comprise a small proportion of inert binder, i.e. less than 15% by weight.

The loss on ignition measured at 900° C. is in the range 4.0% to 7.7% by weight, preferably in the range 4.7% to 6.7% by weight.

More preferably, the adsorbent has a very low proportion of inert binder, i.e. less than 5% by weight; the adsorbent is termed "binderless".

The preferred desorbant is para-diethylbenzene, however other desorbants such as toluene, para-difluorobenzene or diethylbenzenes as a mixture may also be suitable. Preferably, para-diethylbenzene is recommended because it is easy to recover by distillation and has a high affinity for the adsorbent.

In accordance with another feature of the process of the invention, the operating conditions for the adsorption step are as follows:

the temperature is 100° C. to 250° C., preferably 120° C. to 180° C.;

the pressure is between the bubble-point pressure of xylenes at the temperature of the process and $30 \times 10^5$ Pa (1 bar=$10^5$ Pa);

the ratio of the flow rates of desorbant to feed is 0.7 to 2.5;

the recycle ratio is in the range 2.5 to 12, preferably 3.5 to 6. The recycle ratio is defined as the ratio between the mean flow rate flowing in the various beds of adsorbent and the flow rate of feed injected into this adsorbent;

the duration of the cycle followed by the adsorbers is in the range 14 to 30 minutes, preferably in the range 18 to 23 minutes;

the mean linear velocity with respect to the empty reactor is in the range 0.7 cm/s to 1.4 cm/s, preferably in the range 0.85 cm/s to 1.1 cm/s;

the water content in the liquid phase is maintained at a content in the range 70 to 140 ppm (by weight), preferably in the range 80 to 120 ppm (by weight).

The configuration (mean number of beds per zone) of the process of the invention may be with a fixed number of beds (the shifts of the various injection or withdrawal points are simultaneous) or a variable number of beds. In this latter case, the shifts of the 2 injection points and the 2 withdrawal points are not simultaneous so as to obtain numbers of beds per zone which are not integral on average over a cycle.

The configuration of a unit can be defined by defining the mean number of beds for a zone j (j being in the range 1 to 4), Nzj, with respect to the total number of beds in the whole of the unit (in the two adsorbers), N total, as follows:

$$Nz1 = (N\text{ total} \times 5/24) \times (1 \pm 0.2);$$

$$Nz2 = (N\text{ total} \times 9/24) \times (1 \pm 0.2);$$

$$Nz3 = (N\text{ total} \times 7/24) \times (1 \pm 0.2);$$

$$Nz4 = (N\text{ total} \times 3/24) \times (1 \pm 0.2);$$

The process of the present invention can be used to obtain a para-xylene yield of more than 90%, preferably more than 95%, and more preferably more than 98%.

The productivity reached by the process of the invention is preferably in the range 80 kg to 200 kg of para-xylene produced per hour per $m^3$ of adsorbent bed, preferably in the range 90 kg to 180 kg of para-xylene produced per hour per $m^3$ of adsorbent bed, still more preferably in the range 90 kg to 160 kg of para-xylene produced per hour per $m^3$ of bed of adsorbent.

In the case of remodelling an existing unit, the invention also concerns a method for transforming a high purity simulated moving bed para-xylene production process with 24 beds containing two adsorbers of 12 beds into a process in accordance with the present invention.

This method consists of modifying (also known as remodelling) an existing facility with a view to increasing its productivity by reducing the total volume of adsorbent without modifying the production capacity of the unit.

The method of the invention consists of removing beds of adsorbent located either at the head or at the bottom of the adsorber. To this end, the head plates and/or bottom plates of at least one of the adsorbers is displaced by a height corresponding to the number of beds of adsorbent removed from the head and/or the bottom. The intermediate networks and plates corresponding to the removed beds are also removed. The inlet/outlet devices corresponding to the removed networks are plugged. The head octopus manifolds and/or bottom octopus manifolds are modified so as to respectively supply the head plate and/or collector plate of the bottom plate when the position thereof has been modified.

The system for controlling and regulating the feed and desorbant injection flow rates and the extract and raffinate withdrawal flow rates is adapted so as to be able to manage the remodelled process of the invention with a reduced number of beds.

when the supply or withdrawal of fluids over all of the plates of the existing 24 bed process is provided by a plurality of programmed on-off valves, no supplemental modifications have to be made to the supply and the withdrawal networks which have not been removed;

when the supply or withdrawal of fluids over all of the plates of the existing 24-bed process is provided by using a rotary multi-way valve, this latter will be replaced:

a) either by a device for supplying or withdrawing fluids over the set of plates of the process via a plurality of programmed on-off valves;

b) or by a new rotary multi-way valve which is adapted to a process with a reduced number of beds.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application No. 12/02.869, filed Oct. 26, 2012, are incorporated by reference herein.

EXAMPLES

The invention will be better understood from the three examples below, the first corresponding to a prior art unit and the next two to units in accordance with the invention.

Example 1

Process in Accordance with the Prior Art

Consider a SCC unit constituted by 24 beds with a length of 1.1 m and an internal radius of 1.05 m, with a feed injection, a desorbant injection, an extract withdrawal and a raffinate withdrawal.

The adsorbent employed was a zeolitic BaX type solid and the desorbant was para-diethylbenzene. The temperature was 175° C. and the pressure was 15 bars.

The water content was 95 ppm (by weight).

The feed was composed of 21.6% para-xylene, 20.8% ortho-xylene, 47.9% meta-xylene and 9.7% ethylbenzene.

The SCC unit was constituted by two adsorbers each with twelve beds. The beds were separated by distributor plates. An injection network and a withdrawal network were associated with each distributor plate. The rinsing device used was the modulated bypass fluid flow rate device as described in patent WO 2010/020715.

The synchronicity was 100% in each zone.

The shifts for the various injection and withdrawal points were simultaneous. The beds were distributed in the 4 chromatographic zones in accordance with the configuration: 5/9/7/3.

The feed and desorbant injection flow rates (defined by assuming a reference temperature of 40° C.) were as follows:

0.637 m$^3$·min$^{-1}$ for the feed;

0.805 m$^3$·min$^{-1}$ for the desorbant.

In addition, the flow rate for zone 4 was 1.963 m$^3$·min$^{-1}$ and the extract withdrawal flow rate was 0.414 m$^3$·min$^{-1}$. The switch period employed was 68.0 seconds.

By simulation, a para-xylene purity of 99.86% was obtained with a yield of para-xylene of 98.4%, and with a productivity of 75.5 kg$_{PX}$·h$^{-1}$·m$^{-3}$.

Example 2

Process in Accordance with the Invention Obtained by Remodelling an Existing Unit with Two Adsorbers Each with 12 Beds Starting from the prior art unit described in example 1, remodelling was to be carried out into a unit in accordance with the invention constituted by two adsorbers each with 8 beds.

The process was remodelled from a 24 bed process constituted by two adsorbers each with 12 beds. In each adsorber, the two head beds and the two bottom beds were removed. Each bed was 1.1 m long and had an internal radius of 1.05 m.

The intermediate networks and plates corresponding to the removed beds were removed.

The inlet/outlet devices corresponding to the removed networks were plugged.

The head octopus manifolds and/or bottom octopus manifolds were modified so as to respectively supply the head plate and/or collector plate from the bottom plate, when the position thereof had been modified.

The adsorbent employed was a zeolitic BaX type solid and the desorbant was para-diethylbenzene. The temperature was 175° C. and the pressure was 15 bars.

The feed was composed of 21.6% para-xylene, 20.8% ortho-xylene, 47.9% meta-xylene and 9.7% ethylbenzene.

Each adsorber was constituted by 8 beds separated by distributor plates.

An injection network and a withdrawal network were associated with each distributor plate. The rinsing device used was the modulated bypass fluid flow rate device as described in patent WO 2010/020715. The synchronicity was 100% in each zone.

The shifts for the various injection and withdrawal points were simultaneous. The beds were distributed in the 4 chromatographic zones in accordance with the configuration: 3/6/5/2.

The feed and desorbant injection flow rates (defined by assuming a reference temperature of 40° C.) were as follows:

0.637 m$^3$·min$^{-1}$ for the feed;

0.805 m$^3$·min$^{-1}$ for the desorbant.

In addition, the flow rate for zone 4 was 1.959 m$^3$·min$^{-1}$ and the extract withdrawal flow rate was 0.414 m$^3$·min$^{-1}$. The switch period employed was 102.0 seconds.

By simulation, a para-xylene purity of 99.83% was obtained with a yield of para-xylene of 98.1%, and with a productivity of 112.9 kg$_{PX}$·h$^{-1}$·m$^{-3}$.

Example 3

New Unit for the Process of the Invention

Consider a unit constituted by two adsorbers, one containing 8 beds, the other containing 7 beds. Each bed was 1.1 m long and had an internal radius of 1.05 m.

The adsorbent employed was a zeolitic BaX type solid and the desorbant was para-diethylbenzene. The temperature was 175° C. and the pressure was 15 bars.

The feed was composed of 21.6% para-xylene, 20.8% ortho-xylene, 47.9% meta-xylene and 9.7% ethylbenzene.

Each adsorber was constituted by beds separated by distributor plates.

An injection network and a withdrawal network were associated with each distributor plate.

The rinsing device used was the modulated bypass fluid flow rate device as described in patent WO 2010/020715. The synchronicity was 100% in each zone.

The shifts for the various injection and withdrawal points were simultaneous.

The beds were distributed in the 4 chromatographic zones in accordance with the configuration: 3/6/4/2.

The feed and desorbant injection flow rates (defined by assuming a reference temperature of 40° C.) were as follows:
0.637 m$^3$·min$^{-1}$ for the feed;
0.805 m$^3$·min$^{-1}$ for the desorbant.

In addition, the flow rate for zone 4 was 1.959 m$^3$·min$^{-1}$ and the extract withdrawal flow rate was 0.414 m$^3$·min$^{-1}$. The switch period employed was 108.8 seconds.

By simulation, a para-xylene purity of 99.81% was obtained with a yield of para-xylene of 97.8%, and with a productivity of 120.4 kg$_{PX}$·h$^{-1}$·m$^{-3}$.

These examples provide a good illustration of the advantage of the process of the invention which can be used to maintain the same flow rate of para-xylene production while reducing the quantity of adsorbent solid necessary compared with a process in accordance with the prior art, whether this result is obtained with a new unit or by remodelling an existing unit.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separating xylenes by simulated counter-current (SCC) using two adsorbers, the process containing a bed wherein the total number of beds Nt is at most 22, and having a line for introducing feed (F), a line for introducing eluent (D), a line for withdrawing extract (E) and a line for withdrawing raffinate (R) and being divided into 4 chromatographic zones defined as follows:
   zone 1: para-xylene desorption zone, included between the injection of desorbant D and the removal of extract E;
   zone 2: isomers of para-xylene desorption zone, included between the removal of the extract E and the injection of the feed to be fractionated F;
   zone 3: para-xylene adsorption zone, included between the injection of the feed and the withdrawal of the raffinate R;
   zone 4: zone located between the withdrawal of the raffinate and the injection of the desorbant;
the two adsorbers functioning in series wherein the last bed of the first adsorber is connected to the first bed of the second adsorber via a line containing a recirculation pump, and the last bed of the second adsorber is connected to the first bed of the first adsorber via a line containing a recirculation pump which is distinct from the preceding pump, and said process operating under the following operating conditions:
   a temperature of 100° C. to 250° C.;
   a pressure in the range between the bubble pressure of the xylenes at the process temperature and 30×10$^5$ Pa (1 bar=10$^5$ Pa);
   a ratio of desorbent to feed flow rates of 0.7 to 2.5;
   a recycle ratio of 2.5 to 12, wherein the recycle ratio is defined as the ratio between the mean flow rate in the various beds of the adsorber to the flow rate of injection of feed into this adsorber;
   a cycle time for the adsorbers in the range 14 to 30 minutes;
   a mean linear velocity with respect to the empty reactor in the range 0.7 cm/s to 1.4 cm/s;
   a water content in the liquid phase maintained at an amount in the range 70 to 140 ppm by weight.

2. A process according to claim 1, in which the total number Nt of beds distributed over the two adsorbers is at most 18.

3. A process according to claim 1, in which the number of beds N1 of the first adsorber and the number N2 of the second adsorber are equal.

4. A process according to claim 1, in which the number of beds N1 of the first adsorber is equal to 12.

5. A process for separating xylenes by simulated counter-current (SCC) using an existing unit composed of two adsorbers each containing 12 beds, which unit is transformed to finally contain a bed wherein the total number of beds Nt is at most 22, and said unit having a line for introducing feed (F), a line for introducing eluent (D), a line for withdrawing extract (E) and a line for withdrawing raffinate (R) and being divided into 4 chromatographic zones defined as follows:
   zone 1: para-xylene desorption zone, included between the injection of desorbant D and the removal of extract E;
   zone 2: isomers of para-xylene desorption zone, included between the removal of the extract E and the injection of the feed to be fractionated F;
   zone 3: para-xylene adsorption zone, included between the injection of the feed and the withdrawal of the raffinate R;
   zone 4: zone located between the withdrawal of the raffinate and the injection of the desorbant;
the two adsorbers functioning in series wherein the last bed of the first adsorber is connected to the first bed of the second adsorber via a line containing a recirculation pump and the last bed of the second adsorber is connected to the first bed of the first adsorber via a line containing a recirculation pump which is distinct from the preceding pump, the Nt beds constituting a compact assembly in that there are no void spaces which are capable of accepting a bed existing between the Nt beds, in which process the plugged inlets and outlets are entirely located above the head plate and which operates at the following conditions:
   a temperature of 100° C. to 250° C.;
   a pressure in the range between the bubble pressure of the xylenes at the process temperature and 30×10$^5$ Pa (1 bar=10$^5$ Pa);
   a ratio of desorbent to feed flow rates of 0.7 to 2.5;
   a recycle ratio of 2.5 to 12, wherein the recycle ratio is defined as the ratio between the mean flow rate in the various beds of the adsorber to the flow rate of the injection of feed into said adsorber;
   a cycle time for the adsorbers in the range 14 to 30 minutes;
   a mean linear velocity with respect to the empty reactor in the range 0.7 cm/s to 1.4 cm/s;
   a water content in the liquid phase maintained at an amount in the range 70 to 140 ppm by weight.

6. A method for remodelling a simulated moving bed para-xylene production process composed of two adsorbers of 12 beds in series, in a process in accordance with claim 5, comprising:
   displacing the head and/or bottom plates of at least one of the adsorbers by a height corresponding to the number of beds of adsorbents removed at the head and/or the bottom;

removing the intermediate networks and plates corresponding to the removed beds;

plugging the inlet/outlet devices corresponding to the removed networks;

modifying the head octopus manifold so as to supply said head plate.

7. The process according to claim 1, wherein the operating temperature is 120° C. to 180° C.

8. The process according to claim 1, wherein the recycle ratio is 3.5 to 6.

9. The process according to claim 1, wherein in the cycle time for the adsorbers is 18 to 23 minutes.

10. The process according to claim 1, wherein in the mean linear velocity with respect to the empty reactor 0.85 cm/s to 1.1 cm/s.

11. The process according to claim 1, wherein the operating water content in the liquid phase is maintained at 80 to 120 ppm by weight.

12. The process according to claim 5, wherein the operating temperature is 120° C. to 180° C.

13. The process according to claim 5, wherein the recycle ratio is 3.5 to 6.

14. The process according to claim 5, wherein in the cycle time for the adsorbers is 18 to 23 minutes.

15. The process according to claim 5, wherein in the mean linear velocity with respect to the empty reactor 0.85 cm/s to 1.1 cm/s.

16. The process according to claim 5, wherein the water content in the liquid phase is maintained at 80 to 120 ppm by weight.

* * * * *